US009668860B2

(12) United States Patent
Kudlik et al.

(10) Patent No.: US 9,668,860 B2
(45) Date of Patent: Jun. 6, 2017

(54) DEVICE AND METHOD FOR HEART VALVE REPAIR

(75) Inventors: Nachman Kudlik, Tel Aviv (IL); Demitry Pevnay, Modi'n (IL)

(73) Assignee: The Medical Research, Infrastructure, and Health Services Fun of Tel Aviv Medical Center (IL)

( * ) Notice: Subject to any disclaimer, the term of this patent is extended or adjusted under 35 U.S.C. 154(b) by 205 days.

(21) Appl. No.: 14/110,077

(22) PCT Filed: Apr. 4, 2012

(86) PCT No.: PCT/IL2012/050126
§ 371 (c)(1),
(2), (4) Date: Oct. 4, 2013

(87) PCT Pub. No.: WO2012/137208
PCT Pub. Date: Oct. 11, 2012

(65) Prior Publication Data
US 2014/0031926 A1    Jan. 30, 2014

Related U.S. Application Data

(60) Provisional application No. 61/471,497, filed on Apr. 4, 2011, provisional application No. 61/473,873, filed on Apr. 11, 2011.

(51) Int. Cl.
*A61F 2/36* (2006.01)
*A61F 2/24* (2006.01)
(Continued)

(52) U.S. Cl.
CPC ........ *A61F 2/2454* (2013.01); *A61B 17/0401* (2013.01); *A61F 2/2457* (2013.01);
(Continued)

(58) Field of Classification Search
CPC .... A61F 2/2427; A61F 2/2454; A61F 2/2457; A61F 2/2466; A61F 2/2463;
(Continued)

(56) References Cited

U.S. PATENT DOCUMENTS 6,332,893 B1   12/2001   Mortier et al.
7,347,870 B1    3/2008   Andrieu et al.
(Continued)

FOREIGN PATENT DOCUMENTS

WO        03001893 A2      1/2003
WO     2004112658 A1     12/2004
(Continued)

*Primary Examiner* — Richard Louis
(74) *Attorney, Agent, or Firm* — Wood, Phillips, Katz, Clark & Mortimer

(57) ABSTRACT

The invention provides a device (50) and system for treating a heart valve having an anchor (54, 56) and one or more sutures attached to the anchor. The anchor has an expanded deployed configuration and a low caliber undeployed configuration. A delivery in a heart includes catheter and a needle slidable in the lumen of the catheter. The distal end of the catheter is inserted through the myocardium of the heart until the catheter tip is juxtaposed to the underside of the valve leaflet to be treated. The leaflet is then pierced with tip of the needle. The needle is pushed until the anchor in its undeployed configuration passes through the needle tip and is released from the catheter. The anchor is then brought to its deployed configuration on one or both surfaces of the valve leaflet.

10 Claims, 9 Drawing Sheets

(51) Int. Cl.
*A61B 17/04* (2006.01)
*A61B 17/00* (2006.01)
*A61B 90/00* (2016.01)

(52) U.S. Cl.
CPC .. *A61F 2/2466* (2013.01); *A61B 2017/00349* (2013.01); *A61B 2017/00557* (2013.01); *A61B 2017/00862* (2013.01); *A61B 2017/00867* (2013.01); *A61B 2017/0417* (2013.01); *A61B 2017/0464* (2013.01); *A61B 2090/3912* (2016.02); *A61B 2090/3925* (2016.02); *A61F 2/2463* (2013.01)

(58) Field of Classification Search
CPC ........ A61B 17/0401; A61B 2090/3925; A61B 2090/3912; A61B 2017/00349; A61B 2017/00867; A61B 2017/0417; A61B 2017/00557; A61B 2017/00862; A61B 2017/0464
See application file for complete search history.

(56) References Cited

U.S. PATENT DOCUMENTS

| | | | |
|---|---|---|---|
| 8,029,518 B2 | 10/2011 | Goldfarb et al. | |
| 8,043,368 B2 | 10/2011 | Crabtree | |
| 8,062,313 B2 | 11/2011 | Kimblad | |
| 2004/0158308 A1* | 8/2004 | Hogendijk | A61F 2/88 623/1.11 |
| 2005/0075654 A1* | 4/2005 | Kelleher | 606/151 |
| 2005/0119735 A1 | 6/2005 | Spence et al. | |
| 2005/0261684 A1* | 11/2005 | Shaolian et al. | 606/61 |
| 2007/0118151 A1* | 5/2007 | Davidson | A61B 17/00234 606/144 |
| 2007/0265700 A1* | 11/2007 | Eliasen et al. | 623/2.1 |
| 2008/0009888 A1* | 1/2008 | Ewers et al. | 606/151 |
| 2008/0228223 A1* | 9/2008 | Alkhatib | A61B 17/0401 606/221 |
| 2009/0012557 A1* | 1/2009 | Osypka | A61B 17/0057 606/213 |
| 2009/0276038 A1 | 11/2009 | Tremulis et al. | |
| 2010/0249919 A1* | 9/2010 | Gillinov | A61F 2/2427 623/2.11 |
| 2011/0307055 A1* | 12/2011 | Goldfarb et al. | 623/2.11 |
| 2012/0283643 A1* | 11/2012 | Li et al. | 604/175 |

FOREIGN PATENT DOCUMENTS

| | | |
|---|---|---|
| WO | 2008112237 A2 | 9/2008 |
| WO | 2013/003228 A1 | 1/2013 |

\* cited by examiner

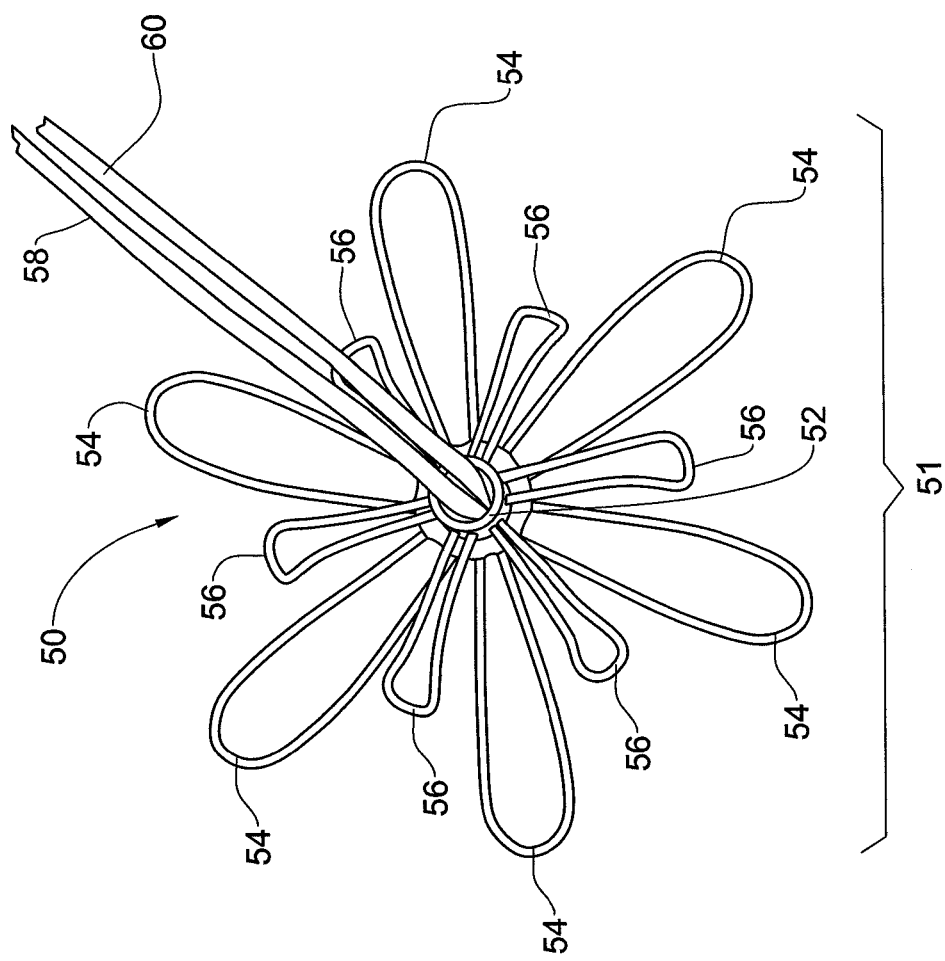

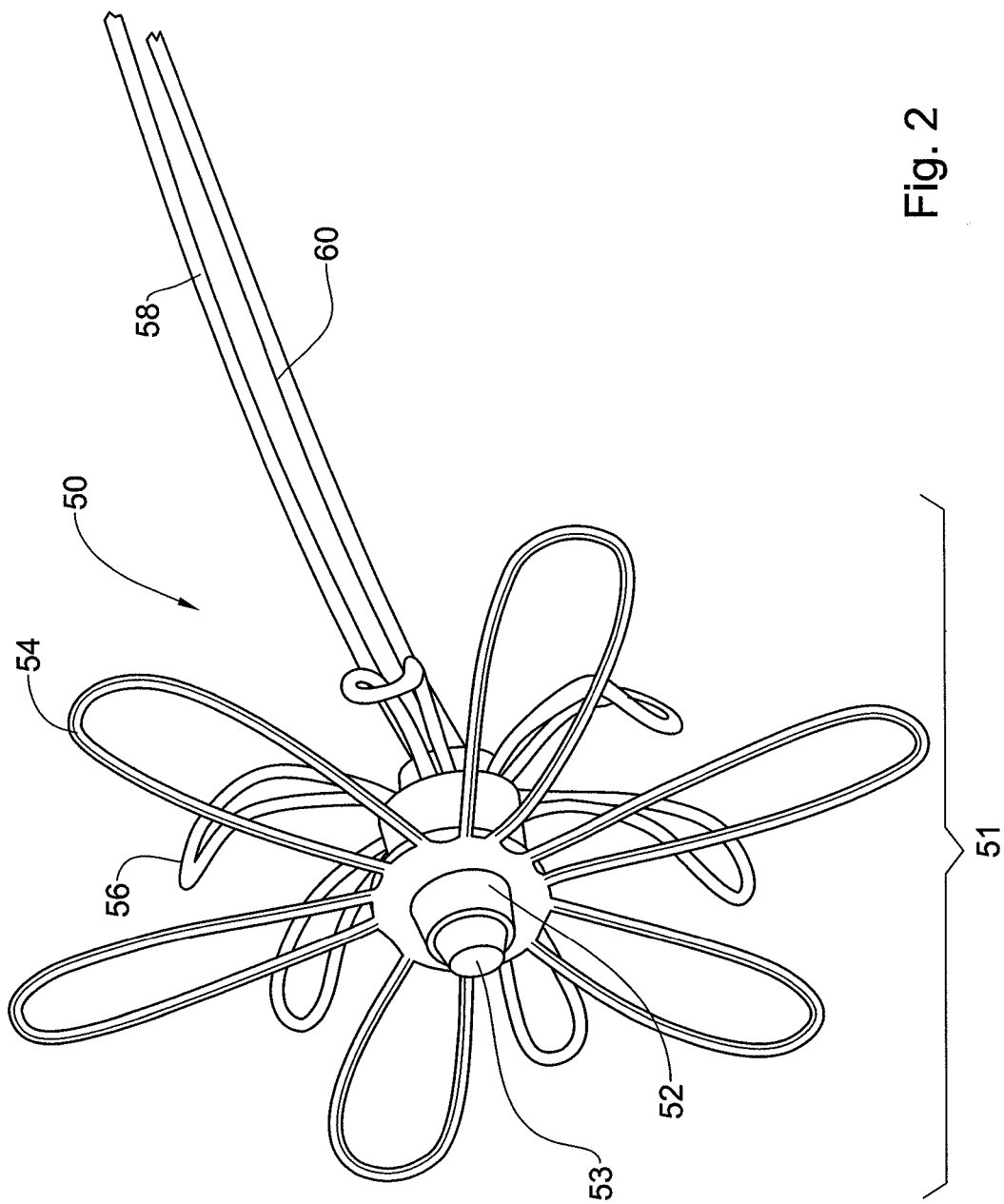

DEVICE AND METHOD FOR HEART VALVE REPAIR

FIELD OF THE INVENTION

This invention relates to medical devices, and more specifically to such devices for treating a heart valves.

BACKGROUND OF THE INVENTION

In the heart, the mitral valve is located between the left atrium and the left ventricle, while the tricuspid valve is located between the right atrium and the right ventricle. Each valve consists of thin leaflets, located between the atrium and the ventricle. The valve leaflets are attached to the inner wall of the ventricle by a series of fibers called chordae. In a healthy heart, when the ventricles contract during systole, the valve leaflets are apposed and thus prevent backflow of blood from the ventricle into the atrium. When the ventricles relax during diastole, the valve opens to allow blood to flow from the atrium into the ventricle.

In mitral valve prolapse, the chordaes have become elongated due to myxomatous degeneration in which collagen in the heart structures forms abnormally and causes thickening, enlargement, and redundancy of the leaflets and chordae. In addition this process may causes rupture of chordae. Under these conditions, the leaflets prolapse (flap backwards into the left atrium) during systole when the ventricles contract, allowing regurgitation of blood through the valve from the ventricle into the atrium. When severe, mitral regurgitation leads to heart failure and abnormal heart rhythms.

Mitral valve prolapse is the most common heart valve abnormality, affecting five to ten percent of the world population. Significant (moderate to severe) mitral regurgitation is much less common. For example, in one study of two million untreated people in the U.S., moderate or severe mitral regurgitation was found to occur in about 2-3 percent of people Surgery is required for people with severe mitral regurgitation. Guidelines from the American Heart Association and European Society of Cardiology define a person as having severe chronic mitral regurgitation based upon echocardiogram measurements of the heart, heart valves, and blood flow. Mitral valve surgery is a major, open-heart, surgical procedure. The heart is arrested during critical parts of the operation, while oxygenated blood is pumped throughout the body with a heart-lung machine. A small part of the heart is then opened to expose the mitral valve.

Methods for non-invasive or minimally invasive mitral valve prolapse repair have been developed.

One method for treating heart valve prolapse involves binding together the two leaflets along the free edges of the leaflets using a clip. A method and system for suturing valve leaflets is disclosed, for example, in U.S. Pat. No. 8,062,313 to Kimblad. A clip for holding together valve leaflets is disclosed, for example, in U.S. Pat. No. 8,029,518 to Goldfarb et al.

Another method of valve repair involves introducing one or more artificial filaments to replace torn chordate. The filaments, sometimes referred to as "neochordae", are attached at one end to a valve leaflet and at another end to cardiac tissue. A system of this type is disclosed, for example, in U.S. Pat. No. 8,043,368 to Crabtree. These methods require reliable determination of the required length of the neochordae to be introduced, which can be difficult to obtain in a beating heart. In most systems of this type it is difficult to adjust the lengths of the neochordae after deployment.

SUMMARY OF THE INVENTION

In one of its aspects, the present invention provides a device for treating a mitral or tricuspid valve. The device of the invention comprises an anchor having an expanded configuration in which the anchor is deployedon one or both sides of the prolapsed area of a valve leaflet to be treated, and a low caliber configuration in which the anchor is delivered to the site of its deployment. One or more sutures are attached to the anchor. After deployment of the anchor on the valve leaflet being treated, the sutures pass ventricle wall and are then sewn outside the ventricle wall to function as prosthetic chordae, as explained below. The proper length of the artificial chordae can be obtained under echocardiography.

The anchor may have any form that allows the anchor to be applied to one or both of the leaflet surfaces.

In its second aspect, the present invention provides a delivery system for delivering the device of the invention to the site of its deployment in the body. The delivery system comprises a needle into which the device of the invention can be inserted with the anchor in its undeployed configuration. The delivery system further comprises a catheter dimensioned to receive the needle, and a pusher that is used to push the device through the needle, as explained below.

In use, device of the invention in its undeployed configuration is inserted into the needle and the needle is inserted into the catheter or thess. The tube is inserted through a chest incision, and into the ventricle via apex until the echo guided tip of the tube is just below the prolapsed area of the leaflet to be treated. The device is then pushed in the needle until the tip of the needle pierces the valve leaflet being treated. The anchor is then released from the needle and allowed to attain its deployed configuration on one or both sides of the leaflet being treated. Attainment of the deployed configuration may occur spontaneously upon release of the anchor from the tube (for example, if the anchor is made from a resiliently flexible material), or upon a temperature transition, in the case of a anchor formed from a shape memory alloy such as Nitinol. The anchor may be coated, for example, with pericardium or various drugs such as antibiotics.

After deployment of the anchor, the sutures are tied outside the left ventricle wall so as to allow the sutures to function as prosthetic chordate.

Thus, in one of its aspects, the invention provides a device for treating a heart valve comprising:
 (a) an anchor having an expanded deployed configuration and a low caliber undeployed configuration; and
 (b) one or more sutures attached to the anchor.

In the device of the invention, the anchor portion may comprise a central hub from which extend two or more wire loops.

The anchor in the deployed configuration may comprise a first set of one or more wire loops lying in a first plane and a second set of one or more wire loops not lying in the first plane. The second set of wire loops may curved towards the first plane.

In the low caliber undeployed configuration, the first set of loops may collapsed away from the filaments and the second set of loops may be collapsed towards the filaments.

The anchor may comprise comprises a resiliently flexible wire ring and the anchor may further comprise one or more cross elements in the wire ring.

The anchor may comprise a wire rod and the sutures may be attached to the wire rod.

In another of its aspects, the invention provides a system for treating a heart valve comprising:
 (a) A device for treating a heart valve comprising:
  (i) an anchor having an expanded deployed configuration and a low caliber undeployed configuration; and
  (ii) one or more sutures attached to the anchor;
 (b) a delivery catheter having a catheter lumen having proximal end and a distal end; and
 (c) a needle slidable in the catheter lumen, the needle having a needle lumen dimensioned to receive the device in the low caliber configuration of the device, the needle further having a sharp tip.

The system of the invention may comprise a rod configured to push the device in the needle lumen towards the distal end of the catheter. The distal end of the catheter may be provided with a spiral wire.

The distal end of the catheter may be provided with an inflatable balloon that is visible in echocardiography.

The invention also provides a method for treating a heart valve comprising:
 (a) providing a system for treating a heart valve comprising:
  i) A device for treating a heart valve comprising:
   an anchor having an expanded deployed configuration and a low caliber undeployed configuration; and
   one or more sutures attached to the anchor;
  ii) a delivery catheter having a catheter lumen having proximal end and a distal end;
  iii) a needle slidable in the catheter lumen, the needle having a needle lumen dimensioned to receive the device in the low caliber configuration of the device, the needle further having a sharp tip; and
  iv) a rod configured to push the device in the needle lumen towards the distal end of the catheter.
 (b) inserting the device into the delivery system;
 (c) inserting the distal end of the catheter through myocardium of the heart, until the catheter tip is juxtaposed to the underside of the leaflet;
 (d) piercing the leaflet with the sharp tip of the needle;
 (e) pushing the rod towards the tip of the needle until the anchor in its undeployed configuration passes through the needle tip and is released from the catheter;
 (f) bringing the anchor to it deployed configuration on one or both surfaces of the valve leaflet.

BRIEF DESCRIPTION OF THE DRAWINGS

In order to understand the disclosure and to see how it may be carried out in practice, embodiments will now be described, by way of non-limiting example only, with reference to the accompanying drawings, in which:

FIG. 1 shows a device for treating a heart valve leaflet from a first perspective in accordance with one embodiment of the invention;

FIG. 2 shows the device of FIG. 1 from a second perspective;

DETAILED DESCRIPTION OF EMBODIMENTS

Figure 3:
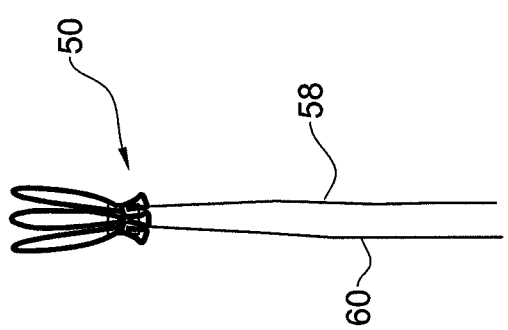
FIG. 3 shows the device of FIG. 1 in an undeployed configuration.

FIGS. 1 to 3 show a device 50 for treating a heart valve in accordance with one embodiment of the invention. The device 50 has an expanded configuration shown from different perspectives in FIGS. 1 and 2 in which the device 50 is deployed in a heart chamber, as explained below. The device 50 also has a low caliber undeployed configuration, shown in FIG. 3, which is used during delivery of the device 2 to a heart valve.

The device 50 has an anchor portion 51 comprising a central hub 52 from which extend a plurality of loops 54 and 56. The hub 52 is a tube that is completely closed at the distal end of the tube, for example, by plugging the distal end of the tube with an adhesive 53. In the embodiment of FIGS. 1 to 3, there are 12 loops. This is by way of example only, and the device 50 may have any number of loops are required in any application. The device 50 includes six coplanar loops 54 and another six loops 56 located below the plane of the loops 54 and which curve upwards towards the plane of the loops 54. The loops 54 and 56 are made from a single piece of wire that may be for example, a Nitinol™ wire having a diameter of about 0.2 mm. The anchor may be coated with bovine pericardium in order to enhance integration of the anchor in the leaflet.

Two sutures 58 and 60 are attached at one end to the hub 52 and extend away from the anchor portion. The sutures 58 and 60 may be, for example, GoreTex ePTFE fibers.

In the compressed configuration shown in FIG. 3, the flat loops 54 and 56 are collapsed upwards away from the hub 52 and filaments 58 and 60, while the curved loops 56 are folded downwards towards the hub and filaments 58 and 60, so that the device 50 attains a low caliber suitable for delivery to the site of its deployment in a heart chamber.

Figure 5:
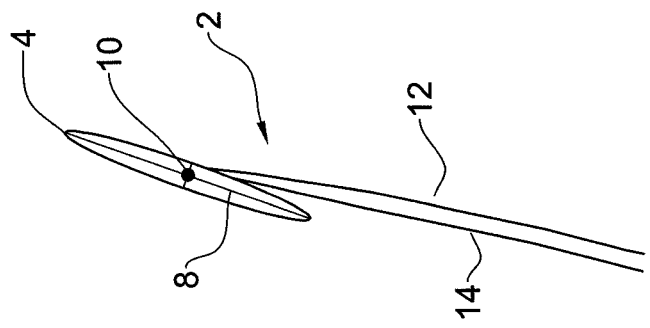
FIG. 5 shows the device of FIG. 4 in an undeployed configuration.
Figure 4:
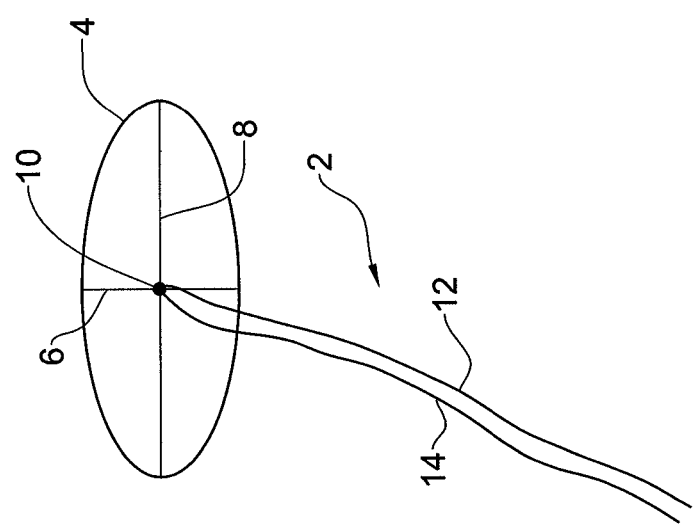
FIG. 4 shows a device having a wire loop for treating a heart valve leaflet in accordance with another embodiment of the invention.

FIGS. 4 and 5 show a device 2 for treating a heart valve in accordance with another embodiment of the invention. The device 2 has an anchor portion 4 comprising an elliptical wire ring, with one or more cross elements. Two cross elements 6 and 8 are shown in FIGS. 4 and 5. This is by way of example only, and the anchor 4 may any number of cross elements. The device 2 has an expanded configuration shown in FIG. 4 in which the device 2 is deployed in a heart chamber and a low caliber undeployed configuration, shown in FIG. 5, which is used during delivery of the device 2 to a heart valve. A pair of sutures 12 and 14 are tied at one end to the cross elements 6 and 8. The other ends of the sutures 12 and 14 are free prior to deployment of the device 2 in a heart valve, as explained below. The sutures may be, for example, Gortex sutures.

The anchor 4 is formed from a deformable material that allows the anchor 4 in the deployed configuration (FIG. 4) to be collapsed into the undeployed configuration (FIG. 5) prior to delivery of the device, and then to regain the deployed configuration after proper positioning in the heart. The wires of the anchor 4 may be made, for example, from a biocompatible elastic or spring-like material, such as silicone rubber, stainless steel or Nitinol. Alternatively, the wires of the anchor 4 may be made from a shape memory alloy (one-way or two-way), in which case the anchor 4 can alternate between the deployed configuration and the undeployed configuration by an appropriate transition of temperature, as is known in the art of shape memory alloys. The anchor may be coated with bovine pericardium in order to enhance integration of the anchor in the leaflet.

Figures 6, 7:
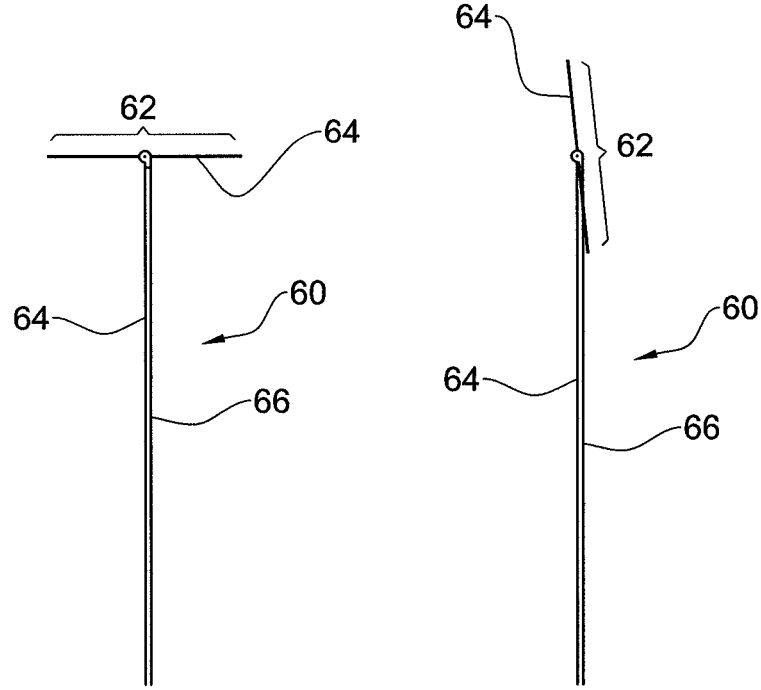
FIG. 6 shows a having a rod device for treating a heart valve leaflet in accordance with another embodiment of the invention.
FIG. 7 shows the device of FIG. 6 in an undeployed configuration.

FIGS. 6 and 7 show a device 60 for treating a heart valve in accordance with another embodiment of the invention. The device 60 has an anchor portion 62 comprising wire rod 64. The rod 64 may be made, for example, from a biocompatible elastic or spring-like material, such as silicone rubber, stainless steel or Nitinol. The device 60 has an expanded configuration shown in FIG. 6 in which the device 60 is deployed in a heart chamber and a low caliber undeployed configuration, shown in FIG. 7, which is used during delivery of the device 60 to a heart valve. A pair of sutures 64 and 66 are tied to the rod 64 at the center of the rod 64. The other ends of the sutures 64 and 66 are free prior to deployment of the device 60 in a heart valve, as explained below. The sutures may be, for example, Gortex sutures. The rod 64 may be coated with bovine pericardium in order to enhance integration of the anchor in the leaflet.

Figure 8:
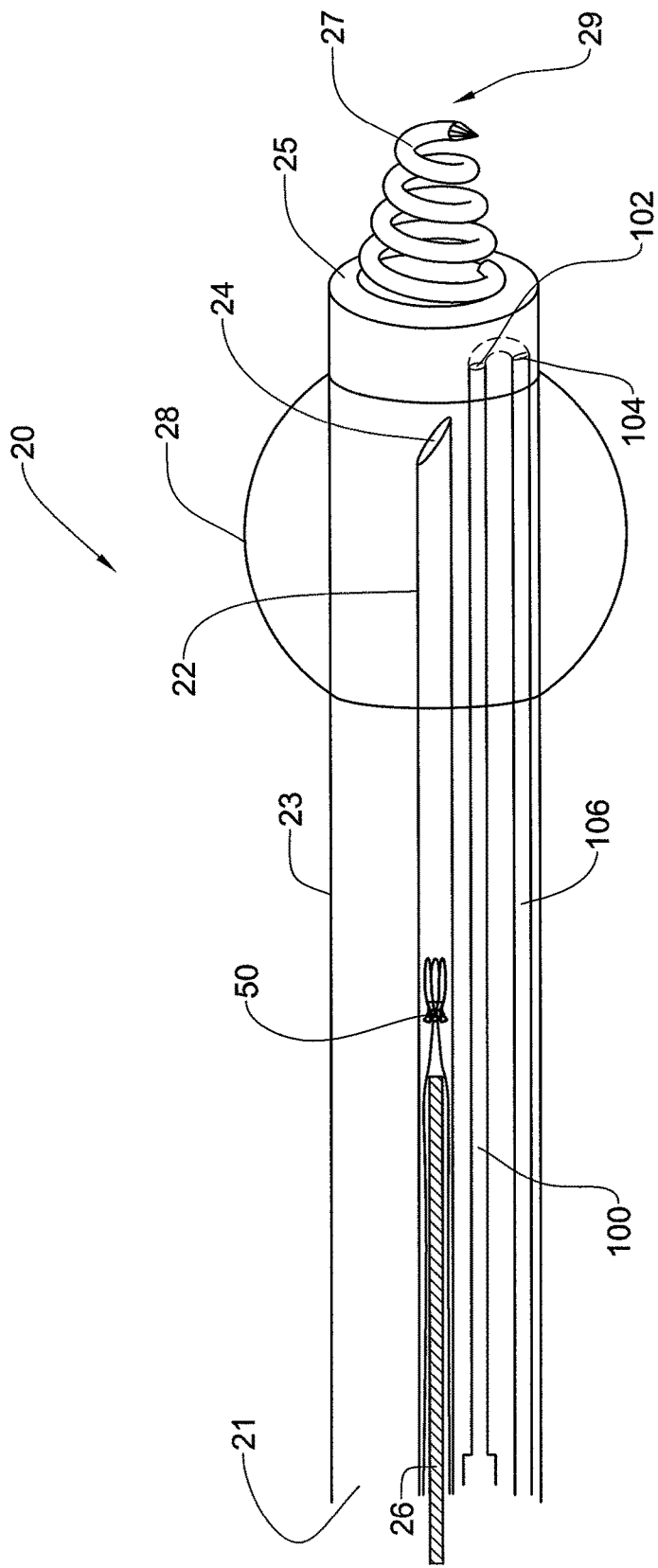
FIG. 8 shows a delivery system for delivering and deploying a device of the invention.

FIG. 8 shows the device 50 of FIGS. 1 and 2 in its undeployed configuration inserted into a delivery system 20. The delivery system 20 comprises a delivery catheter 23 having a proximal end 21 and a distal end 29, that is visible under echocardiography. The delivery system 20 also comprises a needle 22 into which the device 50 is inserted in its undeployed configuration. The needle 22 terminates at its distal end in a sharp tip 24 that is used to pierce the valve leaflet being treated during deployment of the device 2. The delivery system 20 further comprises a pushing rod 26 dimensioned to be slidable within the needle 22. The rod 26 is longer than the needle 22 so as to be accessible at the proximal end of the delivery system 20 during delivery of the device 50. The rod 26 is used to push the device 50 through the tip 24 of the needle 22 during deployment of the device 50. The catheter 23 terminates in a blunt tip 25 at its distal end. Attached to the blunt tip 25 is a spiral wire 27 configured to screw into the underside of the valve leaflet being treated, as explained below.

Also at the distal end of the catheter 23 is a torroidal shaped balloon 28 that is visible in echocardiography. A delivery tube is provided with a Luer fitting for attachment of a syringe containing a liquid such as sterilized water or saline. The liquid is delivered to the balloon 28 via the delivery tube 100 and enters the balloon 28 through one or more apertures 102. As the balloon 28 is fulled with the liquid, and residual air in the balloon or excess liquid is forced out of the balloon 28 through a second set of one or more apertures 104 into a return tube 106 to the proximal end of the catheter 23. The delivery tube 100 and the return tube 106 may be continuous with each other. This allows complete removal of any air in the balloon 28.

Deployment of the device of the invention for the treatment of a prolapsed mitral valve will now be described with reference to the device 50 shown in FIGS. 1 and 2, it being self-evident that other embodiments of the device of the invention may be deployed in a similar fashion.

FIG. 9 shows a method for deploying the device 50 for treatment of a prolapsed mitral valve. FIG. 9a shows a cut away view of a left ventricle 30 including a posterior mitral valve leaflet 32 and an anterior mitral valve leaflet 34. Malocclusion of the leaflets 32 and 34 is evident by a space 36 between the leaflets due to elongation of the chordae 35. For deployment of a device 50, the device 50 is inserted into the delivery system 20, as shown in FIG. 8. The tip 25 of the catheter 23 is inserted through the myocardium 38, until the catheter tip 25 is juxtaposed to the underside of the leaflet 32. Movement of the delivery system in the left ventricle, and deployment of the device may be monitored by echocardiography of the balloon 23. Bleeding can be controlled by a purse string suture. With the heart still beating or while using frequent heart pacing, the catheter 23 is rotated so as to screw the spiral wire 27 into the underside of the valve leaflet 32. Then as shown in FIG. 9b, the sharp tip 24 of the needle 22 is made to pierce through the leaflet 32.

Figure 9A:
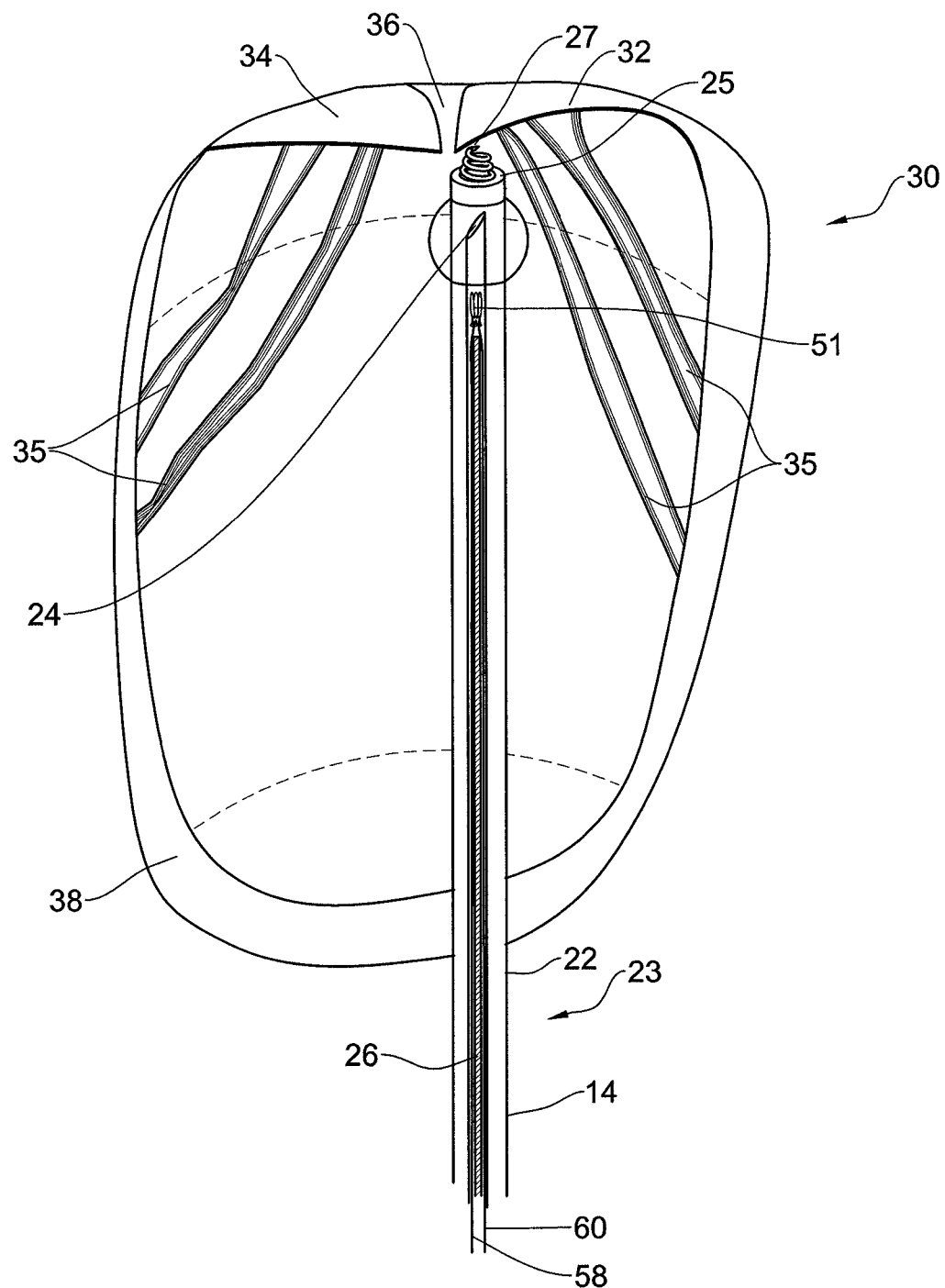
FIG. 9a shows delivery of a device of the invention to a heart valve leaflet.
Figure 9B:
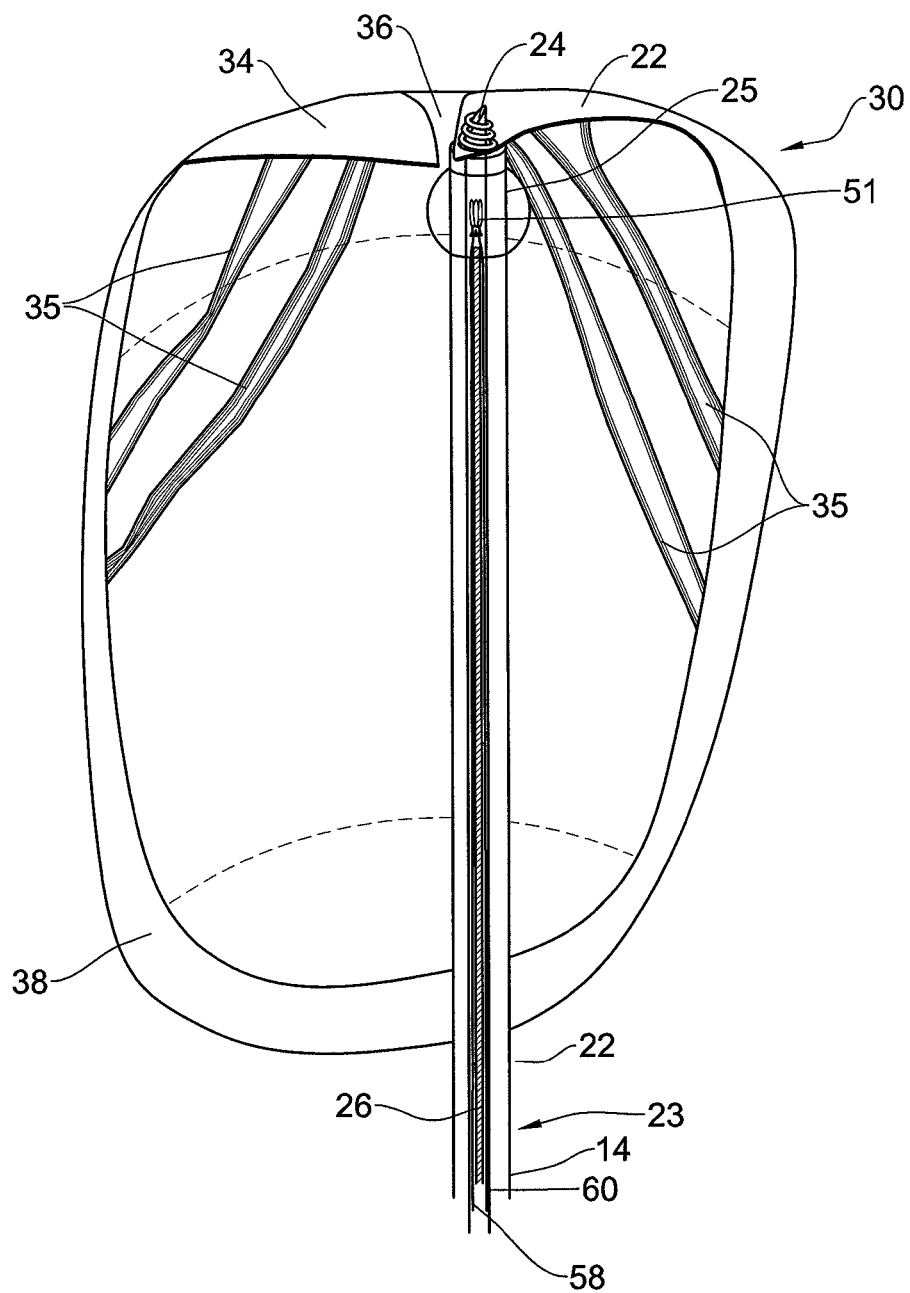
FIG. 9b shows piercing a heart valve leaflet with a needle.
Figure 9C:
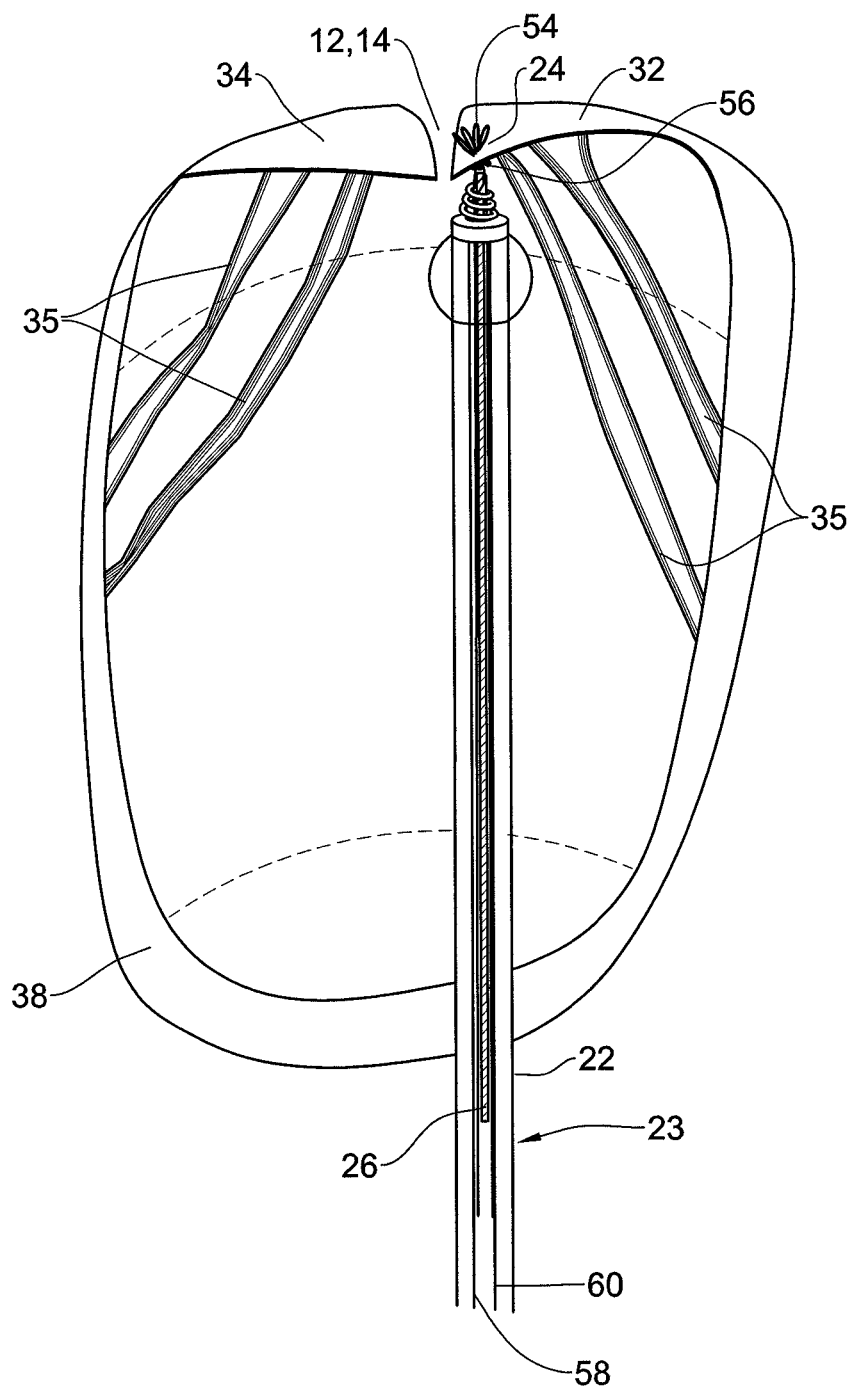
FIG. 9c shows a first stage in the deployment of a device of the invention at a heart valve.
Figure 9E:
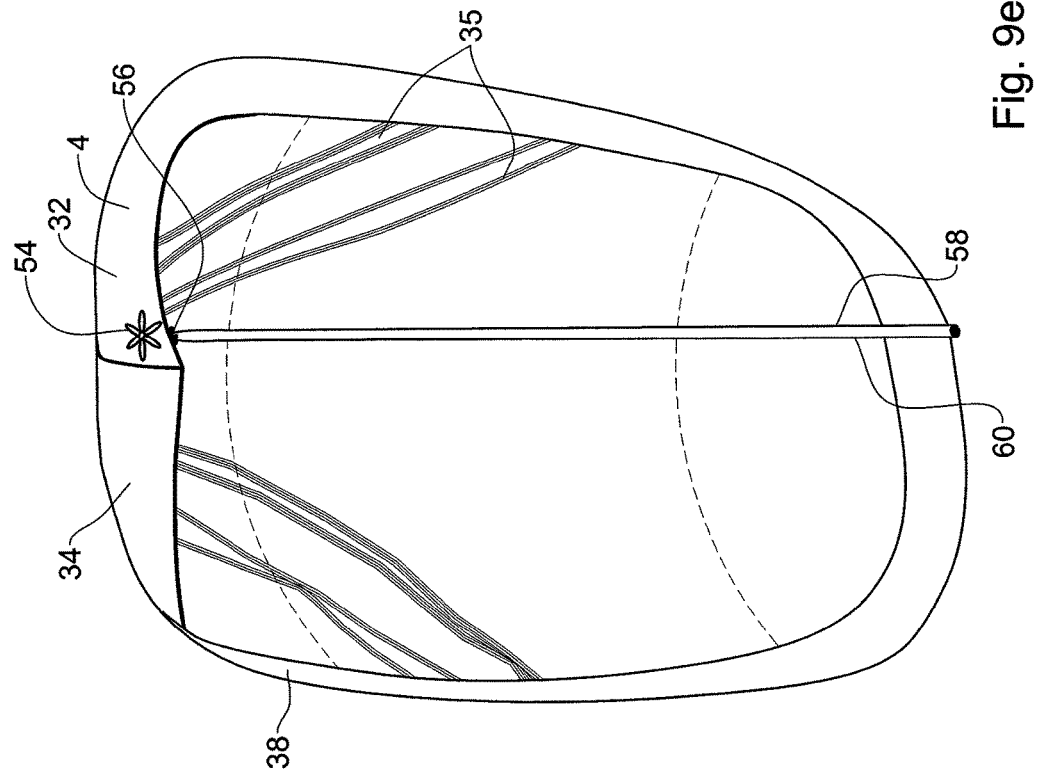
FIG. 9e shows a device of the invention after deployment in a heart valve and removal of the delivery device.
Figure 9D:
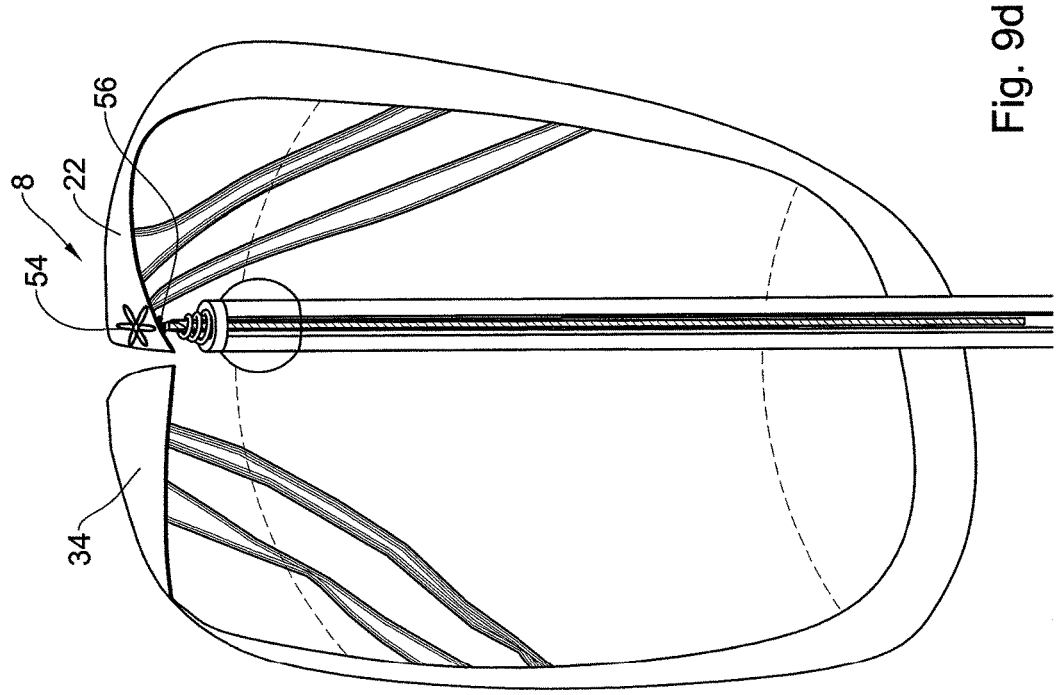
FIG. 9d shows a second stage in the deployment of a device of the invention at a heart valve.

Now, as shown in FIG. 9c, the rod 26 is pushed towards the tip 24 of the needle causing the anchor region 51 in its undeployed configuration to pass through the needle tip 24 and to be released from the catheter 23 with the upper loops 54 positioned in the left atrium above the leaflet 32 and the curved loops 56 positioned in the ventricle below the leaflet 32. At this point the anchor 51 is allowed to attain its deployed configuration (FIG. 9d). This may occur spontaneously upon release of the anchor from the tube 22 (for example, if the anchor is made from a resiliently flexible material), or upon a temperature transition, in the case of a anchor formed from a shape memory alloy such as Nitinol. As the delivery system 20 is removed from the left ventricle, the sutures 12 and 14 are pulled downwards the proper length of neochordaes may be monitored by echocardiography. The sutures continue to be pulled until the leaflets are apposed, and the space 36 is eliminated (FIG. 9e), so that the mitral regurgitation has been corrected. When the correct length of the sutures has been determined, the sutures are fixed to the myocardium 38 so that the sutures can function as prosthetic chordaes.

The invention claimed is:

1. A device for treating a heart valve comprising:
   (a) an anchor portion comprising
      a central hub configured for plugging a piercing formed in the valve leaflet, wherein said central hub is closed at one end thereof; and
      a first plurality of closed wire loops and a second plurality of closed wire loops extending from the central hub;
         the anchor portion having an expanded deployed configuration and a low caliber undeployed configuration the anchor portion configured for anchoring the device onto a valve leaflet in the expanded deployed configuration, such that when in situ (i) the central hub is positioned in the piercing, (ii) the first plurality of closed wire loops is positioned above the valve leaflet and (iii) the second plurality of closed wire loops is positioned below the valve leaflet; and
   (b) one or more sutures attached to the anchor portion at the central hub, the sutures extending away from the first plurality of closed wire loops and from the second plurality of closed wire loops, the sutures being configured and of a length sufficient to enable the sutures to function as prosthetic chordates when fixed to the myocardium.

2. The device according to claim 1, wherein, in the low caliber undeployed configuration, said first plurality of closed wire loops are collapsed away from the sutures and said second plurality of closed wire loops are collapsed towards the sutures.

3. The device according to claim 1, wherein each one of said first plurality of closed wire loops and said second plurality of closed wire loops comprises two or more said closed wire loops.

4. The device according to claim 3, wherein the anchor portion in the deployed configuration comprises said first plurality of closed wire loops lying in a first plane and said second plurality of closed wire loops not lying in the first plane.

5. The device according to claim 4, wherein said second plurality of closed wire loops are curved towards the first plane.

6. A system for treating a heart valve comprising:
(a) a device for treating a heart valve comprising:
  (i) an anchor portion comprising
    a central hub configured for plugging a piercing formed in the valve leaflet, wherein said central hub is closed at one end thereof; and
    a first plurality of closed wire loops and a second plurality of closed wire loops extending from the central hub;
      the anchor portion having an expanded deployed configuration and a low caliber undeployed configuration the anchor portion configured for anchoring the device onto a valve leaflet in the expanded deployed configuration, such that when in situ (i) the central hub is positioned in the piercing, (ii) the first plurality of closed wire loops is positioned above the valve leaflet and (iii) the second plurality of closed wire loops is positioned below the valve leaflet; and
  (ii) one or more sutures attached to the anchor portion at the central hub, the sutures extending away from the first plurality of closed wire loops and from the second plurality of closed wire loops, the sutures being configured and of a length sufficient to enable the sutures to function as prosthetic chordates when fixed to the myocardium;
(b) a delivery catheter having a catheter lumen having proximal end and a distal end; and
(c) a needle slidable in the catheter lumen, the needle having a needle lumen dimensioned to receive the device in the low caliber configuration of the device, the needle further having a sharp tip.

7. The system according to claim 6, further comprising a rod configured to push the device in the needle lumen towards the distal end of the catheter.

8. The system according to claim 6, wherein the distal end of the catheter is provided with a spiral wire.

9. The system according to claim 6, wherein the distal end of the catheter is provided with an inflatable balloon that is visible in echocardiography.

10. A method for treating a heart valve comprising:
(a) providing a system for treating a heart valve comprising:
  i) a device for treating a heart valve comprising:
    an anchor portion comprising
      a central hub configured for plugging a piercing formed in the valve leaflet, wherein said central hub is closed at one end thereof; and
      a first plurality of closed wire loops and a second plurality of closed wire loops extending from the central hub;
        the anchor portion having an expanded deployed configuration and a low caliber undeployed configuration, the anchor portion configured for anchoring the device onto a valve leaflet in the expanded deployed configuration, such that when in situ (i) the central hub is positioned in the piercing, (ii) the first plurality of closed wire loops is positioned above the valve leaflet and (iii) the second plurality of closed wire loops is positioned below the valve leaflet; and
      one or more sutures attached to the anchor portion at the central hub, the sutures extending away from the first plurality of closed wire loops and from the second plurality of closed wire loops, the sutures being configured and of a length sufficient to enable the sutures to function as prosthetic chordates when fixed to the myocardium;
  ii) a delivery catheter having a catheter lumen having proximal end and a distal end;
  iii) a needle slidable in the catheter lumen, the needle having a needle lumen dimensioned to receive the device in the low caliber configuration of the device, the needle further having a sharp tip; and
  iv) a rod configured to push the device in the needle lumen towards the distal end of the catheter;
(b) inserting the device into the delivery system;
(c) inserting the distal end of the catheter through myocardium of the heart, until the catheter tip is juxtaposed to the underside of the leaflet;
(d) piercing the leaflet with the sharp tip of the needle;
(e) pushing the rod towards the tip of the needle until the anchor portion in its undeployed configuration passes through the needle tip and is released from the catheter;
(f) bringing the anchor portion to its deployed configuration with said first plurality of closed wire loops on one surfaces of the valve leaflet and with said second plurality of closed wire loops on another surface of the valve leaflet.

* * * * *

UNITED STATES PATENT AND TRADEMARK OFFICE
CERTIFICATE OF CORRECTION

PATENT NO. : 9,668,860 B2
APPLICATION NO. : 14/110077
DATED : June 6, 2017
INVENTOR(S) : Nachman Kudlik and Demitry Pevnay It is certified that error appears in the above-identified patent and that said Letters Patent is hereby corrected as shown below:

On the Title Page

(73) "The Medical Research, Infrastructure, and Health Services Fun of Tel Aviv Medical Center (IL)", should be -- The Medical Research, Infrastructure, and Health Services Fund of Tel Aviv Medical Center (IL) --

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*